(12) United States Patent
Sarrafzadeh et al.

(10) Patent No.: US 11,170,310 B2
(45) Date of Patent: Nov. 9, 2021

(54) SYSTEMS AND METHODS FOR AUTOMATIC SEGMENT SELECTION FOR MULTI-DIMENSIONAL BIOMEDICAL SIGNALS

(71) Applicant: The Regents of the University of California, Oakland, CA (US)

(72) Inventors: Majid Sarrafzadeh, Anaheim Hills, CA (US); Mars Lan, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 677 days.

(21) Appl. No.: 14/374,520

(22) PCT Filed: Jan. 25, 2013

(86) PCT No.: PCT/US2013/023295
§ 371 (c)(1),
(2) Date: Jul. 24, 2014

(87) PCT Pub. No.: WO2013/112935
PCT Pub. Date: Aug. 1, 2013

(65) Prior Publication Data
US 2014/0379620 A1 Dec. 25, 2014

Related U.S. Application Data
(60) Provisional application No. 61/590,751, filed on Jan. 25, 2012.

(51) Int. Cl.
*G06N 5/04* (2006.01)
*G06N 20/00* (2019.01)
(Continued)

(52) U.S. Cl.
CPC ............ *G06N 5/047* (2013.01); *A61B 5/369* (2021.01); *A61B 5/7264* (2013.01); *G06F 19/00* (2013.01);
(Continued)

(58) Field of Classification Search
None
See application file for complete search history.

(56) References Cited

U.S. PATENT DOCUMENTS 7,853,317 B2 * 12/2010 Duann ................. A61B 5/0452
600/509
2004/0193064 A1 * 9/2004 Shusterman ......... A61B 5/0452
600/504
(Continued)

FOREIGN PATENT DOCUMENTS

KR 10-2009-0001146 A 1/2009
KR 10-2010-0067363 A 6/2010
(Continued)

OTHER PUBLICATIONS

Bruce et al, Dimensionality Reduction of Hyperspectral Data Using Discrete Wavelet Transform Feature Extraction, 2006.*
(Continued)

*Primary Examiner* — Kamran Afshar
*Assistant Examiner* — Benjamin J Buss
(74) *Attorney, Agent, or Firm* — Foley & Lardner LLP

(57) ABSTRACT

Systems and methods for automatically analyzing and selecting prominent channels from multi-dimensional biomedical signals in order to detect particular diseases or ailments are provided. Such systems and methods may be applied in different ways to obtain numerous benefits, such as lowering of power and processing requirements, reducing an amount of data acquired, simplifying hardware deploy-
(Continued)

ment, detecting non-trivial patterns, obtaining, clinical episode prognosis, improving patient care, and/or the like.

8 Claims, 5 Drawing Sheets

(51) Int. Cl.
    *G16H 50/20*     (2018.01)
    *A61B 5/00*     (2006.01)
    *G06K 9/62*     (2006.01)
    *A61B 5/369*     (2021.01)
    *G06F 19/00*     (2018.01)

(52) U.S. Cl.
    CPC ............ *G06K 9/6228* (2013.01); *G06N 20/00* (2019.01); *G16H 50/20* (2018.01)

(56) References Cited

U.S. PATENT DOCUMENTS

| | | | |
|---|---|---|---|
| 2004/0210147 A1 | 10/2004 | Houben | |
| 2004/0230105 A1* | 11/2004 | Geva | G06F 19/324 600/301 |
| 2005/0113703 A1* | 5/2005 | Farringdon | A61B 5/0428 600/509 |
| 2005/0288600 A1* | 12/2005 | Zhang | A61B 5/0006 600/510 |
| 2009/0265297 A1* | 10/2009 | Misra | G06N 99/005 706/52 |
| 2011/0218823 A1 | 9/2011 | Patton | |
| 2011/0307438 A1* | 12/2011 | Fernandez Martinez | G06N 7/005 706/52 |
| 2012/0123232 A1* | 5/2012 | Najarian | A61B 5/0022 600/345 |
| 2015/0216436 A1* | 8/2015 | Bosl | A61B 5/7264 600/544 |
| 2016/0179599 A1* | 6/2016 | Deshpande | G06F 11/0745 714/807 |

FOREIGN PATENT DOCUMENTS

| | | |
|---|---|---|
| KR | 10-1048763 | 7/2011 |
| WO | WO-2009/025863 | 2/2009 |

OTHER PUBLICATIONS

Gandhi et al, A comparitive study of wavelet families for EEG signal classification, 2011.*
Bsoul et al, Detection of P, QRS, and T Components of ECG Using Wavelet Transformation, 2009.*
Fanelli et al, Prototype of a wearable system for remote fetal monitoring during pregnancy, 2010.*
Ghongade et al, Performance Analysis of Feature Extraction Schemes for Artificial Neural Network Based ECG Classification, 2008.*
Kiatpanichagij et al, Use of supervised discretization with PCA in wavelet packet transformation-based surface electromyogram classification, 2009.*
Kohler et al, The Principles of Software QRS Detection, 2002.*
Zhang et al, QRS Detection Based on Multiscale Mathematical Morphology for Wearable ECG Devices in Body Area Networks, 2009.*
Conradsen et al, Seizure Onset Detection based on a Uni- or Multi-modal Intelligent Seizure Acquisition (UISA/MISA) System, 2010.*
Lal et al, Support Vector Channel Selection in BCI (Year: 2004).*
Williamson et al, Epileptic Seizure Prediction Using the Spatiotemporal Correlation Structure of Intracranial EEG (Year: 2011).*
Bostanov V (2004), "BCI Competition 2003-Data Sets Ib and IIb: Feature Extraction From Event-Related Brain Potentials With the Continuous Wavelet Transform and the t-Value Scalogram", IEEE Transactions on Biomedical Engineering, IEEE Service Center, Piscataway, NJ, USA, vol. 51, No. 6, Jun. 1, 2004, pp. 1057-1061.
Extended European Search Report and Search Opinion for European Application No. 13741359.7 dated Mar. 14, 2016.
International Search Report and Written Opinion dated May 7, 2013, issued in corresponding International Application No. PCT/US2013/023295, filed Jan. 25, 2013, 10 pages.
Summons to Oral Proceedings and Communication from the Examining Division for European Application No. 13741359.7 dated Feb. 27, 2018.

* cited by examiner

SYSTEMS AND METHODS FOR AUTOMATIC SEGMENT SELECTION FOR MULTI-DIMENSIONAL BIOMEDICAL SIGNALS

CROSS-REFERENCE TO RELATED APPLICATION

This application is a National Stage Entry of International Application No. PCT/US2013/023295, filed Jan. 25, 2013, which claims the benefit of U.S. Provisional Application No. 61/590,751, filed Jan. 25, 2012, the entire disclosure of which are hereby incorporated herein.

BACKGROUND

With the recent advent of low-cost, high fidelity, compact, and versatile sensors, it is expected that these sensors will soon become ubiquitous. Many of these sensors will likely have medical applications, such as monitoring various personal health indicators and/or the like. The biomedical signals acquired by these sensors are often in the form of multi-dimensional time series wherein the sensed values are quantized and discretized. One challenge of analyzing such signals stems from the sheer volume of the data. For example, in the case of 64-channel electroencephalographic (EEG) signals sampled at 100 Hz with 16-bit accuracy, the data generated per day is roughly 1 GB, which is a considerably large amount of data to be stored or transmitted by an embedded system even using the latest technology. The problem is further exacerbated by the extremely limited power budget allocated to these sensor systems. It is therefore desirable to have a way to minimize the amount of data acquired by these sensors, without significantly degrading the analysis results.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a computer-implemented method of analyzing signal data is provided. A set of sample data is retrieved by a computing device. The set of sample data includes sample data from a plurality of channels, and is annotated with one or more occurrences of events of interest. The computing device determines one or more channels of the plurality of channels that include patterns associated with occurrences of the events of interest, and the computing device labels the determined one or more channels as useful.

In some embodiments, a nontransitory computer-readable medium having computer-readable instructions stored thereon is provided. The instructions, if executed by one or more processors of a computing device, cause the computing device to perform actions for analyzing signal data. The actions comprise retrieving a set of sample data, wherein the set of sample data includes sample data from a plurality of channels, and is annotated with one or more occurrences of events of interest. The actions further comprise determining one or more channels of the plurality of channels that include patterns associated with occurrences of the events of interest, and labeling the determined one or more channels as useful.

In some embodiments, a system for collecting and analyzing signal data is provided. The system comprises a plurality of sensors, a data store configured to store signal data collected from the plurality of sensors, and a signal processing device communicatively coupled to the data store. The signal processing device is configured to retrieve a set of sample data from the data store, wherein the set of sample data includes sample data from a plurality of channels, each channel associated with at least one sensor of the plurality of sensors, and wherein the set of sample data is annotated with one or more occurrences of events of interest; determine one or more channels of the plurality of channels that include patterns associated with occurrences of the events of interest; and label the determined one or more channels as useful.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

In some embodiments of the present disclosure, high rates of data reduction may be achieved by identifying and limiting data acquisition to signals that relate to the desired analysis outcome. For example, in the case of epileptic patients, only some small segments of the signal from a few selected channels of an EEG sensor system may be used while retaining the ability to reliably predict the onset of seizure. By limiting data acquisition to relevant segments and/or signals, the amount of data to acquire and analyze may be greatly reduced.

In some embodiments, the method uses a large signal database that contains sample signals gathered using a sensor system. These signals are annotated or labeled with the detection target, i.e. the start time, $t_S$, when a disease, ailment, or a clinical episode was detected. For example, a domain expert may use a sensor system to monitor a subject with epilepsy, and may annotate the database of acquired data whenever a seizure onset occurs. The method may be tuned to handle some amount of inaccuracy of $t_S$, though it is assumed here that the annotations are reasonably accurate.

Existing art relies heavily on prior knowledge of the indicative temporal or spectral features of the signals that indicate onset of a clinical episode. While picking features based on expert knowledge may provide accurate predictions, it severely limits the ability of these methods to discover patterns and relationships that are not known to the experts. In embodiments of the present disclosure, no expert knowledge of the signals is assumed. The present method and system may automatically discover interesting long term and short term patterns without human intervention, and may therefore be applied to a wide range of biomedical signals. Also, by mapping these patterns to particular channels of multi-dimensional biomedical signals, embodiments of the present disclosure can also discover complex patterns that span across multiple channels.

In some embodiments, the present disclosure may be implemented as offline analysis and online detection tools for databases that store a large amount of biomedical signals gathered from various sensors attached to or implanted in a subject's body. Examples of sensors may include, but are not limited to, pulse-oximeter sensors, blood pressure sensors, glucose meters or monitors, electrocardiographic sensors, electroencephalographic sensors, and/or the like. The offline analysis tool may be configured to perform a method of analysis, such as the method described below, on the signals stored in the database to detect patterns and channels that best serve as a prognosis for a particular disease or ailment. The information may then be utilized by the online detection tool to analyze incoming signals in real-time. When a similar pattern is detected with high confidence, a corresponding action, such as varying of a drug dosage, issuing an alarm to medical staff, and/or the like, may take place.

Figure 1:
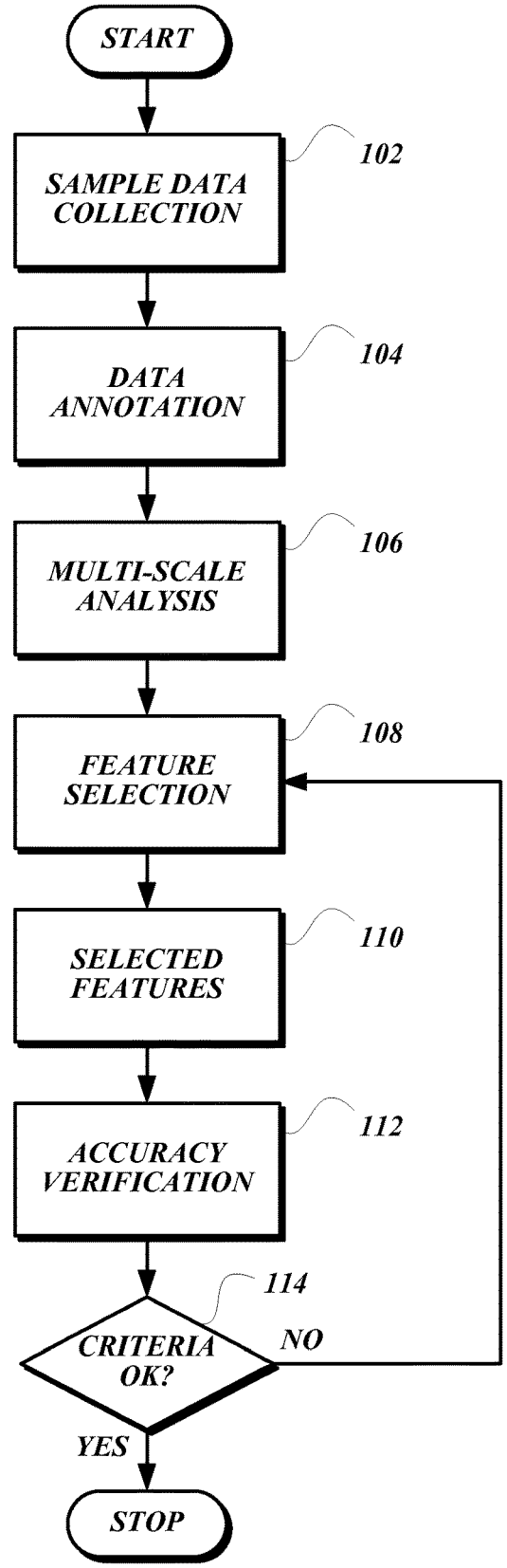
FIG. 1 is a flowchart that illustrates an exemplary embodiment of a method for analyzing signal data, according to various aspects of the present disclosure.

FIG. 1 is a flowchart that illustrates one embodiment of a method of determining significant signals for prediction of an event of interest, according to various aspects of the present disclosure. From a start block, the method proceeds to collect sample data 102, and then to annotate the sample data 104, as discussed above. After $t_S$ is labeled in the database during the data annotation, a pattern discovery algorithm may be executed to identify prominent patterns that serve as precursors for the detection target. In most cases, the precise time and duration of these patterns are unknown in advance. This makes the search space potentially infinite. As a result, some assumptions may be made regarding the earliest possible time, denoted as $t_e$, that such a pattern can occur prior to $t_S$. The search space, S, for the patterns is thus limited to $(t_e, t_S)$. For instance, if the goal is to predict seizure as early as an hour before the onset, S is set to $(t_S-3600, t_S)$.

A multi-scale analysis 106, such as a wavelet transform, may be applied to S. Such a transform may break the signal into joint time-frequency representation using multiple scaled and translated versions of a mother wavelet. Formally, a continuous wavelet transform can be written as:

$$\gamma(s,\tau)=\int f(t)\Psi_{S,S}^*(t)dt$$

where f(t) is the original signal, and $\Psi_{S,t}^*(t)$ is the complex conjugation of a scaled (S) and translated ($\tau$) of mother wavelet $\Psi(t)$. In its simplest form, the mother wavelet may be a square-shaped function:

$$\Psi(t) = \begin{cases} 1, & 0 < t < 1/2 \\ -1, & 1/2 \leq t < 1 \\ 0, & \text{otherwise} \end{cases}$$

Figure 2:
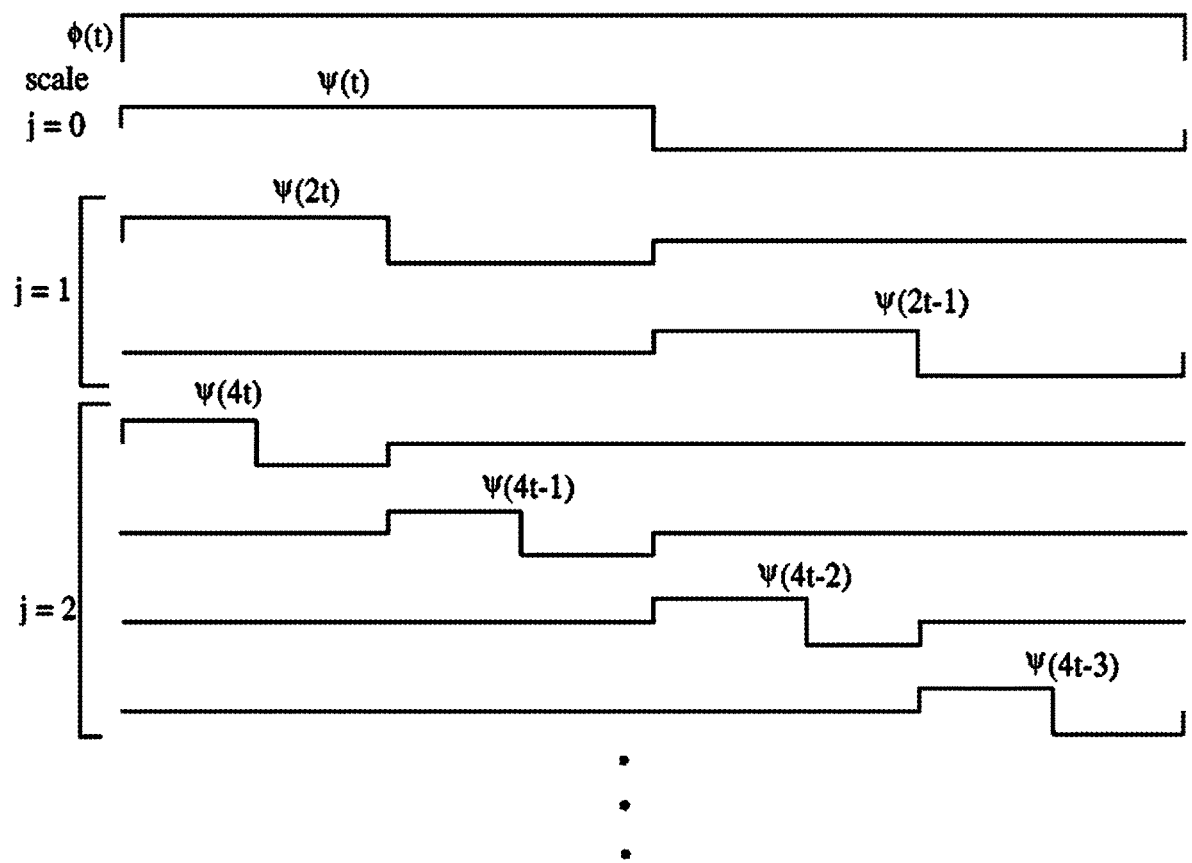
FIG. 2 is a graph that illustrates examples of Haar wavelets at different scales and translations according to various aspects of the present disclosure.

Such a wavelet is known as a Haar wavelet. Its simple structure allows the transformation to be computed quickly and consumes little memory, and so may be a particularly suitable wavelet to be used in some embodiments of the present disclosure. Other suitable types of wavelet transform may instead be used without departing from the scope of the present disclosure. FIG. 2 is a graph that illustrates examples of Haar wavelets at different scales and translations.

Returning to the flowchart of FIG. 1, after the wavelet transform, the signal is now represented by a group of coefficients, which are essentially the scaling factors for each wavelet. The coefficients may be normalized so they range from 0 to 1. Each coefficient is then treated as an independent feature vector of the signal. Depending on the size of S, there can potentially be thousands of features. Using these features directly may over-fit the model of almost all types of machine learning algorithms, which may result in loss of accuracy and general applicability. Consequently, these features may be filtered using a feature selection algorithm 108.

Figure 3:
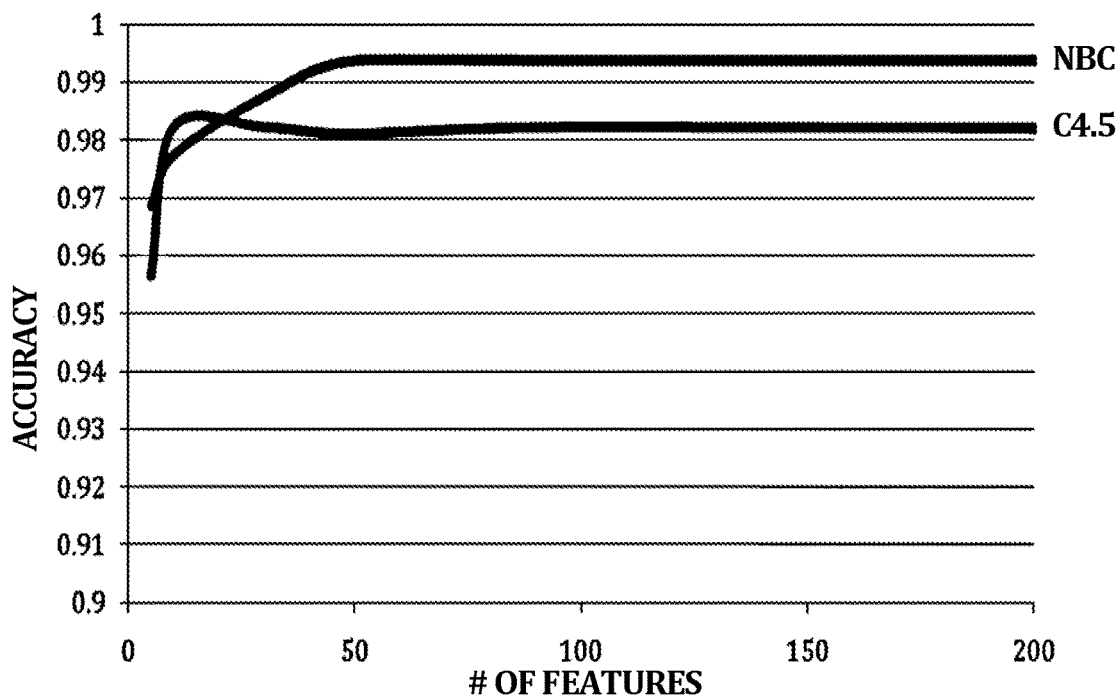
FIG. 3 is a graph that illustrates exemplary accuracy of a naïve Bayes classifier and a C4.5 classifier, according to various aspects of the present disclosure.

Feature selection algorithms may be classified as wrapper-based, embedded, or hybrid. Wrapper-based feature selection algorithms filter features based on their intrinsic relevancy and redundancy. They are classifier agonistic and normally fast to run, compared to the embedded or hybrid algorithms. On the other hand, embedded and hybrid algorithms tend to have a higher accuracy due to repetitive fine-tuning. In some embodiments of the present disclosure, a wrapper-based feature selection algorithm, such as the ones based on information gain or mutual information, may be used due to performance considerations. However, in other embodiments, other feature selection algorithms may be used. Also note that the exact number of top features to select is normally less important than the algorithm itself. As can be seen in FIG. 3, which plots the accuracy of a naïve Bayes classifier (NBC) and a C4.5 classifier, the accuracy of the classifier quickly tapers off after selecting a reasonable small amount of features (<20). Other types of machine learning techniques could be used instead of or in addition to NBC and C4.5.

Returning to the flowchart of FIG. 1, after a set of prominent features are selected 110, they may be mapped back to the corresponding segments of S based on the particular multi-scale analysis used. This allows the features to be identified as long- or short-term patterns. Depending on the particular requirement of the application, patterns that fail to meet one or more predefined criteria may also be removed. Similarly, patterns that are too close or too far from $t_S$ or $t_e$ may also be discarded accordingly.

Figure 4:
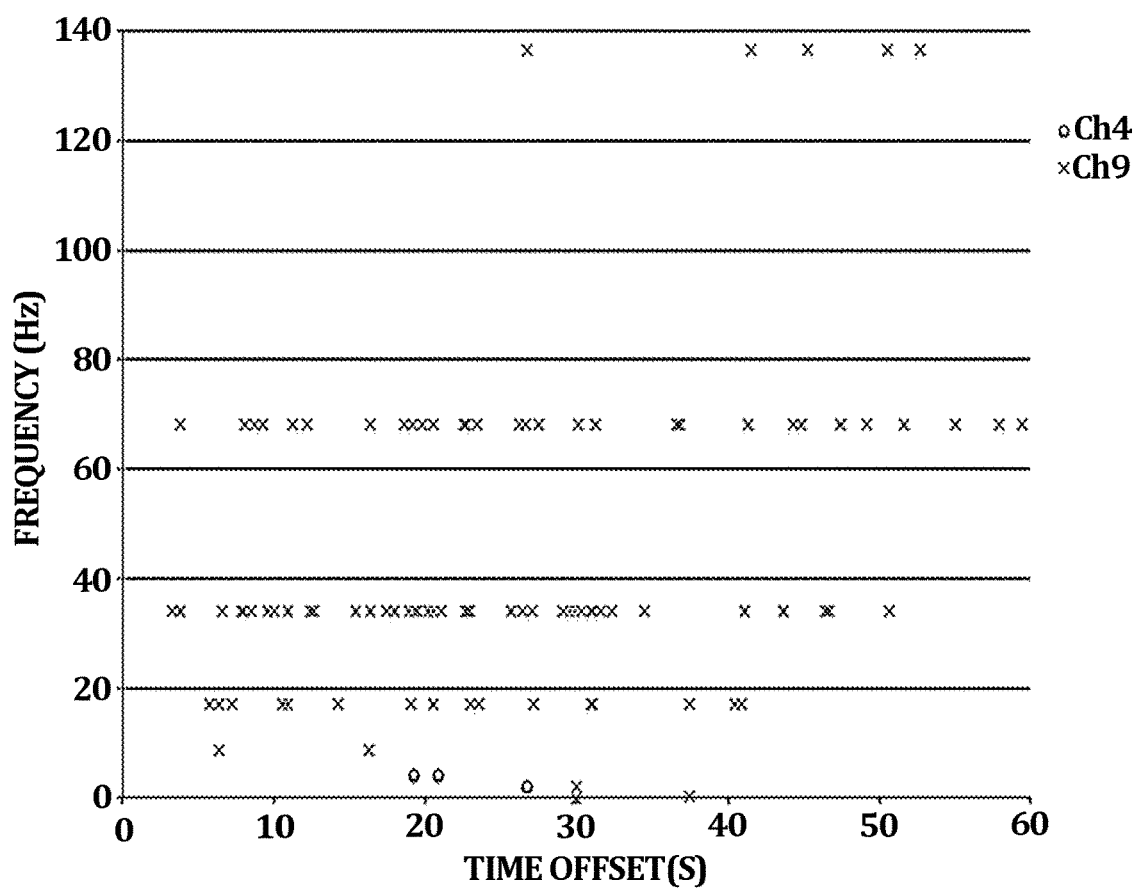
FIG. 4 is a graph that illustrates exemplary prominent features selected from a data store containing signal data representing epileptic seizures, according to various aspects of the present disclosure.

FIG. 4 shows an example of the top-100 features selected from an exemplary data store containing signal data representing epileptic seizures. About one-third of the features have a frequency shorter than 20 Hz, which can be classified as short-term patterns. The remaining features may be used directly as predictors for the occurrence of the event of interest.

Returning to FIG. 1, a supervised learning algorithm, such as Artificial Neural Network (ANN), Supporting Vector Machine (SVM), decision tree, Bayesian Network, and/or the like, may be used to verify the accuracy of these features 112. Alternatively, the corresponding patterns of these features may be isolated and further studied to determine other possible relationships. Next, the channels on which the prominent patterns appear may be labeled as useful. Any unlabeled channels may then be safely discarded or turned off. In other words, the unlabeled channel data may be deleted from the data store, or may not be collected in the future. As illustrated in FIG. 4, the top-100 features in the example data all come from two channels ($F_4$-$C_4$ and $F_{P1}$-

Figure 5:
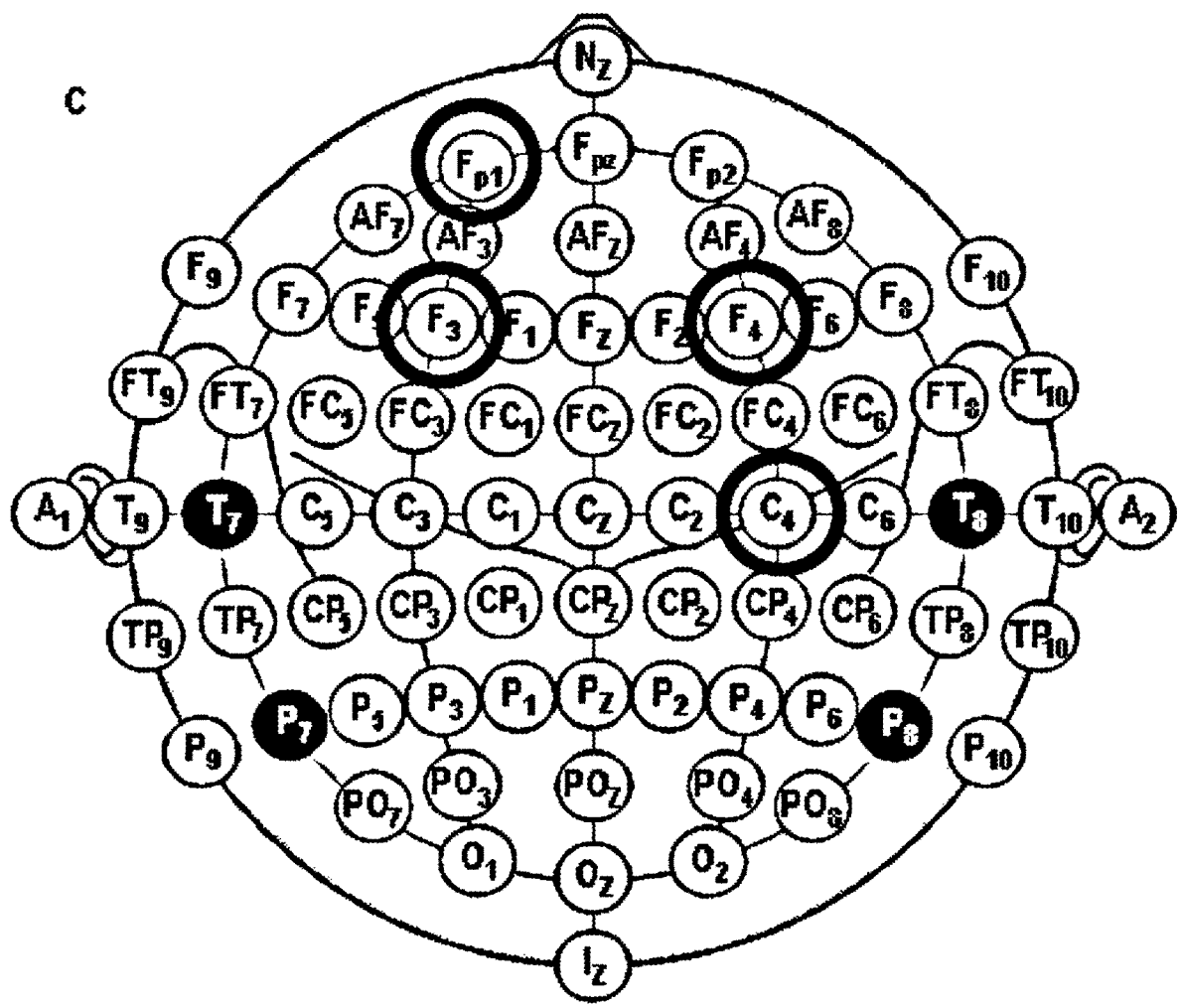
FIG. 5 illustrates an electrode site map used in the collection of EEG data according to various aspects of the present disclosure.

F₃) of the EEG system. These channels are indicated in FIG. 5. The method of FIG. 1 may be repeated several times until the final selection satisfies certain predefined criteria 114, such as power, space, accuracy, and/or the like. The method then proceeds to a stop block and terminates.

Figure 6:
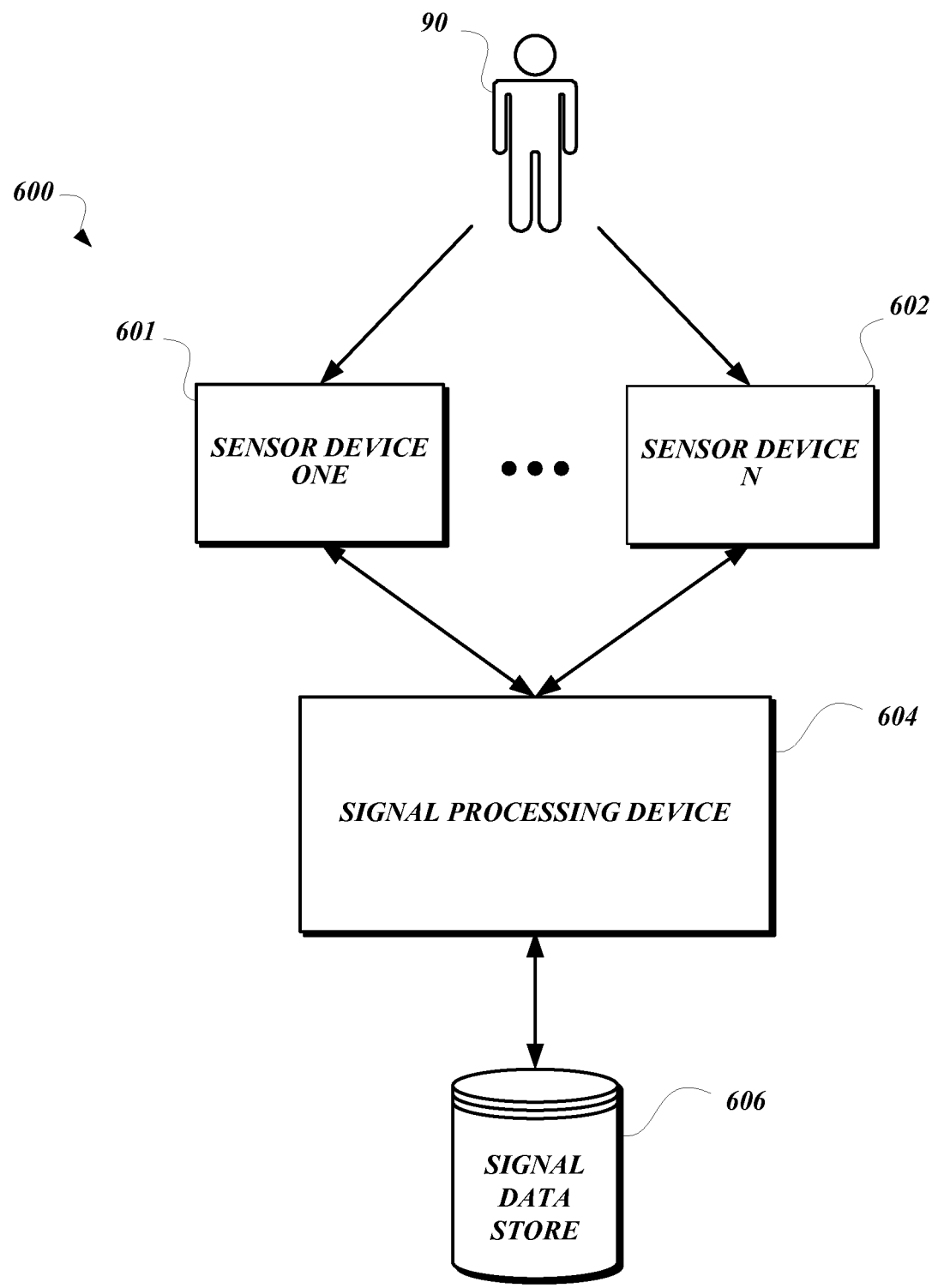
FIG. 6 illustrates a system for collecting, storing, and analyzing signal data, according to various aspects of the present disclosure.

FIG. 6 illustrates one embodiment of a system 600 for collecting and processing physiological signals suitable for use with embodiments of the present disclosure. One or more sensor devices, such as sensor device one 601, sensor device N 602, and the like, are configured to detect physiological conditions in a patient. As discussed above, exemplary sensor devices include, but are not limited to, a respiratory inductance plethysmograph, a pulse oximeter, electrocardiographic sensors, electroencephalographic sensors, blood pressure sensors, glucose meters or monitors and/or the like. Each of the sensor devices 601, 602 generates a signal based on a physical measurement of a physiological state associated with a subject 90, the signal comprising a time series of values.

In one embodiment, the sensor devices 601, 602 are communicatively coupled to a signal processing device 604. The signal processing device 604 is a computing device configured to obtain data generated by the sensor devices 601, 602 and to perform calculations based on the obtained data. In one embodiment, the computing device may include at least one processor, an interface for coupling the computing device to the sensor devices 601, 602, and a non-transitory computer-readable medium. The computer-readable medium has computer-executable instructions stored thereon that, in response to execution by the processor, cause the signal processing device 604 to perform the calculations on the obtained data described above. One example of a suitable computing device is a personal computer specifically programmed to perform the actions described herein. This example should not be taken as limiting, as any suitable computing device, such as a laptop computer, a smartphone, a tablet computer, a cloud computing platform, an embedded device, and the like, may be used in various embodiments of the present disclosure.

The sensor devices 601, 602 may be coupled to the signal processing device 604 by a direct physical connection, such as by a serial cable, a USB cable, and the like. In another embodiment, the sensor devices 601, 602 may be coupled to the signal processing device 604 by a local network connection, such as a Bluetooth connection, a wired local-area network connection, a WIFI connection, an infrared connection, and the like. In yet another embodiment, the sensor devices 601, 602 may be coupled to the signal processing device 604 by a wide area network, such as the Internet, a WiMAX network, a 3G network, a GSM network, and the like. The sensor devices 601, 602 may each include network interface components that couple each sensor device 601, 602 to the signal processing device 604. Alternatively, the sensor devices 601, 602 may each be coupled to a shared networking device via a direct physical connection or a local network connection, which in turn establishes a connection to the signal processing device 604 over a wide area network.

The direct physical connection embodiments and the local area network connection embodiments may be useful in a scenario when the sensor devices 601, 602 are located in close proximity to the signal processing device 604, such as within the same examination room in a clinic. The wide area network embodiments may be useful in a larger telehealth or automated diagnosis application.

In one embodiment, instead of direct transmission of signal data from the sensor devices 601, 602 to the signal processing device 604, the sensor devices 601, 602 may transmit signal data for storage on a storage medium, such as in a signal data store 606. This stored signal data may then be consumed by the signal processing device 604 at a later time for diagnostic purposes, for research purposes, and the like. For example, in some embodiments, the signal processing device 604 may analyze signal data stored in the signal data store 606 in order to identify signals relevant to a desired analysis as described above. As another example, in some embodiments, the signal processing device 604 may receive signal data from the sensor devices 601, 602, and may then only store signal data in the signal data store 606 corresponding to the identified signals. The signal data store 606 may include any suitable type of computer-readable storage medium, such as a hard drive, flash drive, RAM, optical drive, and/or any other suitable medium. Signal data may be stored in the signal data store 606 using any suitable format, such as in a flat file, a spreadsheet, a relational database, and/or any other suitable storage format or technology.

While the preferred embodiment of the disclosure has been illustrated and described, it will be appreciated that various changes can be made therein without departing from the spirit and scope of the present disclosure.

The invention claimed is:

1. A computer-implemented method of analyzing signal data, the method comprising:
retrieving, by a computing device, a set of sample time series data, wherein the set of sample time series data includes sample time series data from a plurality of channels;
annotating the set of sample time series data with an occurrence of an event of interest;
responsive to an indication that the set of sample time series data has been annotated with the occurrence of the event of interest, determining from the set of sample time series data, by the computing device, one or more channels of the plurality of channels that include patterns occurring in time prior to the occurrence of the event of interest based on the annotation;
labeling, by the computing device, the determined one or more channels as useful; and
turning off one or more channels not labeled as useful,
wherein determining one or more channels that include patterns occurring in time prior to the occurrence of the event of interest includes (a) identifying, using the annotation, a search space in the set of sample time series data corresponding to a duration of time up to and including the occurrence of the event of interest and (b) performing a multi-scale analysis of the search space to identify patterns in the set of sample time series data,
wherein performing the multi-scale analysis of the set of sample time series data comprises generating a group of coefficients and normalizing the coefficients to generate features; and wherein determining one or more channels that include patterns occurring in time prior to the occurrence of the event of interest further includes filtering the features using feature selection.

2. The computer-implemented method of claim 1, wherein determining one or more channels that include patterns occurring in time prior to the occurrence of the event of interest further includes verifying the accuracy of the features using supervised learning.

3. The computer-implemented method of claim 1, further comprising:

receiving incoming time series data associated with the one or more channels labeled as useful; and detecting a pattern in the incoming time series data which matches at least one of the patterns occurring in time prior to the occurrence of the event of interest.

4. The computer-implemented method of claim 3, further comprising:

responsive to detecting the pattern in the incoming time series data, issuing an alarm.

5. A nontransitory computer-readable medium having computer-readable instructions stored thereon that, if executed by one or more processors of a computing device, cause the computing device to perform actions for analyzing signal data, the actions comprising:

retrieving, by a computing device, a set of sample time series data, wherein the set of sample time series data includes sample time series data from a plurality of channels;

annotating the set of sample time series data with an occurrence of an event of interest;

responsive to an indication that the set of sample time series data has been annotated with the occurrence of the event of interest, determining from the set of sample time series data, by the computing device, one or more channels of the plurality of channels that include patterns occurring in time prior to the occurrence of the event of interest based on the annotation;

labeling, by the computing device, the determined one or more channels as useful; and turning off one or more channels not labeled as useful, wherein determining one or more channels that include patterns occurring in time prior to the occurrence of the event of interest includes (a) identifying, using the annotation, a search space in the set of sample time series data corresponding to a duration of time up to and including the occurrence of the event of interest and (b) performing a multi-scale analysis of the search space to identify patterns in the set of sample time series data, wherein performing the multi-scale analysis of the set of sample time series data comprises generating a group of coefficients and normalizing the coefficients to generate features; and wherein determining one or more channels that include patterns occurring in time prior to the occurrence of the event of interest further includes filtering the features using feature selection.

6. The computer-readable medium of claim 5, wherein determining one or more channels that include patterns occurring in time prior to the occurrence of the event of interest further includes verifying the accuracy of the features using supervised learning.

7. A system for collecting and analyzing signal data, comprising:

a plurality of sensors;

a data store configured to store time series signal data collected from the plurality of sensors; and a signal processing device communicatively coupled to the data store and configured to:

retrieve a set of sample time series data from the data store, wherein the set of sample time series data includes sample time series data from a plurality of channels, each channel associated with at least one sensor of the plurality of sensors;

annotate the set of sample time series data with an occurrence of an event of interest;

determine, in response to an indication that the set of sample time series data has been annotated with the occurrence of the event of interest, from the set of sample time series data, one or more channels of the plurality of channels that include patterns occurring in time prior to the occurrence of the event of interest based on the annotation; and label the determined one or more channels as useful; and turning off one or more channels not labeled as useful, wherein the signal processing device is configured to determine one or more channels that include patterns occurring in time prior to the occurrence of the event of interest by (a) identifying, using the annotation, a search space in the set of sample time series data corresponding to a duration of time up to and including the occurrence of the event of interest and (b) performing a multi-scale analysis of the search space to identify patterns in the set of sample time series data, wherein the signal processing device is configured to perform the multi-scale analysis of the set of sample time series data by generating a group of coefficients and normalizing the coefficients to generate features; and wherein the signal processing device is configured to determine one or more channels that include patterns occurring in time prior to the occurrence of the event of interest by filtering the features using feature selection.

8. The system of claim 7, wherein the signal processing device is configured to determine one or more channels that include patterns occurring in time prior to the occurrence of the event of interest by verifying the accuracy of the features using supervised learning.

* * * * *